(12) United States Patent  (10) Patent No.: US 8,092,022 B2
Okumura et al.  (45) Date of Patent: Jan. 10, 2012

(54) OPTHALMOLOGY PHOTOGRAPHING APPARATUS

(75) Inventors: Toshiaki Okumura, Tokyo (JP);
Yasuhiro Dobashi, Matsudo (JP);
Yasuhiro Nakahara, Kawasaki (JP);
Hiroshi Aoki, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/788,702

(22) Filed: May 27, 2010

(65) Prior Publication Data

US 2010/0302506 A1  Dec. 2, 2010

(30) Foreign Application Priority Data

Jun. 1, 2009 (JP) ................................. 2009-132356

(51) Int. Cl.
*A61B 3/14* (2006.01)
(52) U.S. Cl. .......................... 351/206; 351/213; 351/221
(58) Field of Classification Search .................. 351/205, 351/206, 210, 221, 213, 216
See application file for complete search history.

(56) References Cited

U.S. PATENT DOCUMENTS 7,794,084 B2 * 9/2010 Masaki et al. ................ 351/206

2006/0082726 A1 * 4/2006 Suzuki .......................... 351/206

FOREIGN PATENT DOCUMENTS

JP  2003-93336 A  4/2003

* cited by examiner

*Primary Examiner* — Huy K Mai
(74) *Attorney, Agent, or Firm* — Canon U.S.A., Inc., IP Division (57) ABSTRACT

A fundus camera includes an illumination unit to illuminate an ocular fundus of a subject's eye, an autofluorescent exciter filter insertable into and retractable from an illumination optical path of the illumination unit, an observation and photographing unit to receive reflection light from the ocular fundus illuminated by the illumination unit and form an ocular fundus image, an autofluorescent barrier filter insertable into and retractable from an observation and photographing optical path, an image capturing unit to capture an ocular fundus image, and a calculation unit to calculate image data, wherein the calculation unit converts the ocular fundus image which is illuminated using the autofluorescent exciter filter and captured by a color image capturing unit as a color image, in a state that no autofluorescent barrier filter is inserted into the observation and photographing unit, into a monochromatic image from specific color data of each of the pixels.

4 Claims, 10 Drawing Sheets

OPTHALMOLOGY PHOTOGRAPHING APPARATUS

BACKGROUND OF THE INVENTION

1. Field of the Invention

The present invention relates to a fundus camera for photographing an ocular fundus of a subject's eye.

2. Description of the Related Art

In order to obtain a clear image of a blood vessel or the like, such a fundus camera is in practical use that an ocular fundus is illuminated through a dedicated narrow-bandwidth bandpass filter, which is referred to as a red free filter, to form a monochromatic image from a color image captured by a color image capture element according to a calculation processing.

Japanese Patent Application Laid-open No. 2003-93336 discusses an electronic endoscope device which produces an effect of a pseudo narrow-bandwidth bandpass filter from a typical RGB color image without providing a dedicated narrow-bandwidth bandpass filter.

In a fundus camera using a red free filter, upon photographing, the dedicated narrow-bandwidth bandpass filter is required and a system for inserting the narrow-bandwidth bandpass filter into an optical path of an illumination unit is also required. Consequently, such a problem arises that the fundus camera using the red free filter comes to have a complex configuration and is expensive.

In Japanese Patent Application Laid-Open No. 2003-93336, since a subject to be examined is a human body, it is premised that a spectral reflectance of the human body is almost constant. However, in Japanese Patent Application Laid-Open No. 2003-93336, it is not generally possible to obtain a specific spectral characteristic from an RGB color image. This is because, there is a case that, even when a color is viewed as the same color as the other color on the RGB color image, the color is actually the color similar to the other color depending on a metamerism caused due to a plurality of wavelengths upon photographing. The metamerism is a phenomenon that physically different colors are viewed as the same colors. For example, if red light and yellow light are extracted from light having various wavelengths and spectrums and are mixed together, thus mixed light becomes an orange color. However, the mixed orange color is a light physically different from an orange color of a single wavelength.

Therefore, a conventional apparatus has an advantage that no optical filter switching system or dedicated filter is required. However, conventional system has a mere pseudo narrow-bandwidth bandpass filter, so that there may be cases that the effect thereof is not sufficient enough with respect to the system using an optical filter, and further no effect can be produced in a specific lesion.

SUMMARY OF THE INVENTION

The present invention relates to a fundus camera of a low cost and with a pseudo narrow-bandwidth bandpass filter.

According to an aspect of the present invention, a fundus camera includes an illumination unit configured to illuminate an ocular fundus of a subject's eye, an autofluorescent exciter filter configured to be insertable into and retractable from an illumination optical path of the illumination unit, an observation and photographing unit configured to receive reflection light from the ocular fundus illuminated by the illumination unit and form an ocular fundus image, an autofluorescent barrier filter configured to be insertable into and retractable from an observation and photographing optical path of the observation and photographing unit, an image capturing unit configured to capture an ocular fundus image formed by the observation and photographing unit, and a calculation unit configured to calculate image data from the image capturing unit, wherein the calculation unit of the fundus camera which can perform both of color image photographing and photofluorography, converts the ocular fundus image which is illuminated using the autofluorescent exciter filter inserted into the illumination unit and captured by a color image capturing unit as a color image, in a state that no autofluorescent barrier filter is inserted into the observation and photographing unit, into a monochromatic image from specific color data of each of the pixels.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention, and together with the description, serve to explain the principles of the invention.

DESCRIPTION OF THE EMBODIMENTS

Various exemplary embodiments, features, and aspects of the invention will be described in detail below with reference to the drawings.

Figure 1:
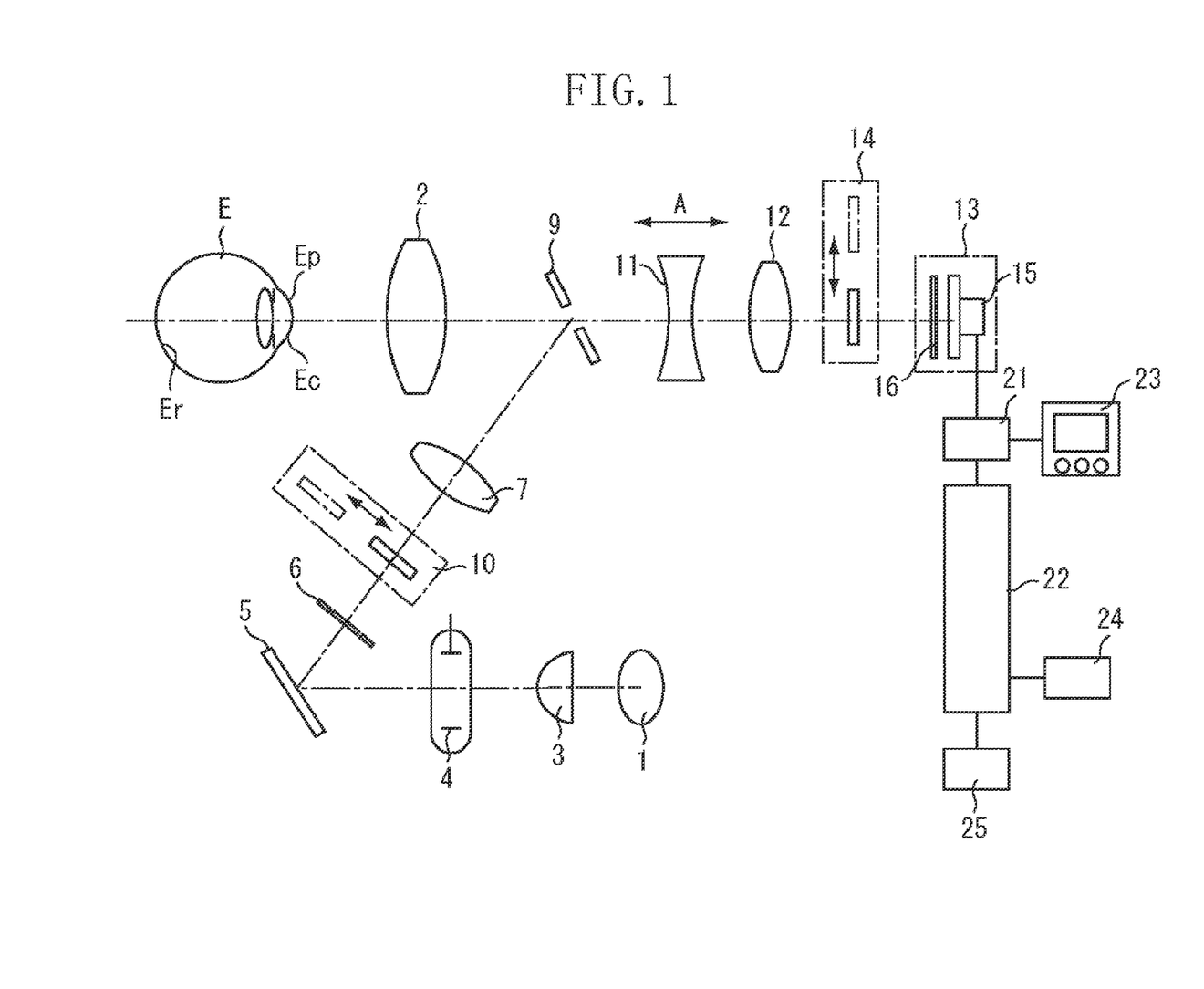
FIG. 1 illustrates a configuration of a fundus camera according to an exemplary embodiment.

FIG. 1 illustrates a configuration of a fundus camera according to an exemplary embodiment. On an optical path from an observation light source 1 to an objective lens 2 placed in front of a subject's eye E, there are arranged a condenser lens 3, a photographic light source 4, a mirror 5, a diaphragm 6 having a ring-shaped opening, a relay lens 7 and a perforated mirror 9 in this order. An autofluorescent exciter filter 10 is insertably/retractably disposed in the optical path between the diaphragm 6 and the relay lens 7. An illumination optical system is configured by the above described components. The autofluorescent exciter filter 10 is inserted into the illumination optical path upon autofluorescent observation and photographing and upon red free photographing, whereas the autofluorescent exciter filter 10 is retreated from the illumination optical system upon color photographing.

On the optical path in a direction that light passes through the perforated mirror 9, there are arranged a focusing lens 11, a photographic lens 12 and a color photographing unit 13 in this order. An autofluorescent barrier filter 14 which blocks autofluorescent exciting light and transmits only fluorescence therethrough is insertably/retractably placed in the optical path between the photographic lens 12 and the color photographing unit 13, so that an observation and photographing optical system is configured. The color photographing unit 13 includes an image sensor 15 and a tri-color separation color filter 16. The autofluorescent barrier filter 14 is inserted into the observation and photographing optical path upon autofluorescent photographing, whereas the autofluorescent barrier filter 14 is retreated from the observation and photographing optical system upon color photographing and upon red free photographing.

An output of the image sensor 15 is connected to a system control unit 22 via an image signal processing unit 21. The image signal processing unit 21 is connected to a display unit 23 which displays an observed image of the subject's eye E for an observation of the subject's eye E. The system control unit 22 is connected to an image recording unit 24 and an operation switch unit 25. Accordingly a control system of the entire fundus camera is configured.

When color image photographing is performed, a light flux emitted from the observation light source 1 passes through the condenser lens 3 and the photographic light source 4 to be reflected by the mirror 5. The light reflected by the mirror passes through the diaphragm 6 and the relay lens 7 and is reflected at an area adjacent to the perforated mirror 9. The light further passes through the objective lens 2 and illuminates the ocular fundus Er of the subject's eye E with visible light. At the time, the autofluorescent exciter filter 10 is retreated from the illumination optical system.

The reflection light from the ocular fundus Er passes through the objective lens 2, a hole of the perforated mirror 9, the focusing lens 11 and the photographic lens 12, and then forms an image on the image sensor 15. At the time, the autofluorescent barrier filter 14 is retreated from the ocular fundus observation and photographing optical system, so that the reflection light of the ocular fundus Er can be observed as it is in the form of an ocular fundus image by the display unit 23.

An examiner moves the apparatus in a back-and-force direction, a horizontal direction, or a vertical direction using a positional index (not illustrated) and an operation unit, while viewing the ocular fundus image, to adjust a position of the apparatus with respect to the subject's eye E. Further, the examiner moves the focusing lens 11 using a focus adjustment index to adjust a focus.

Figure 2A:
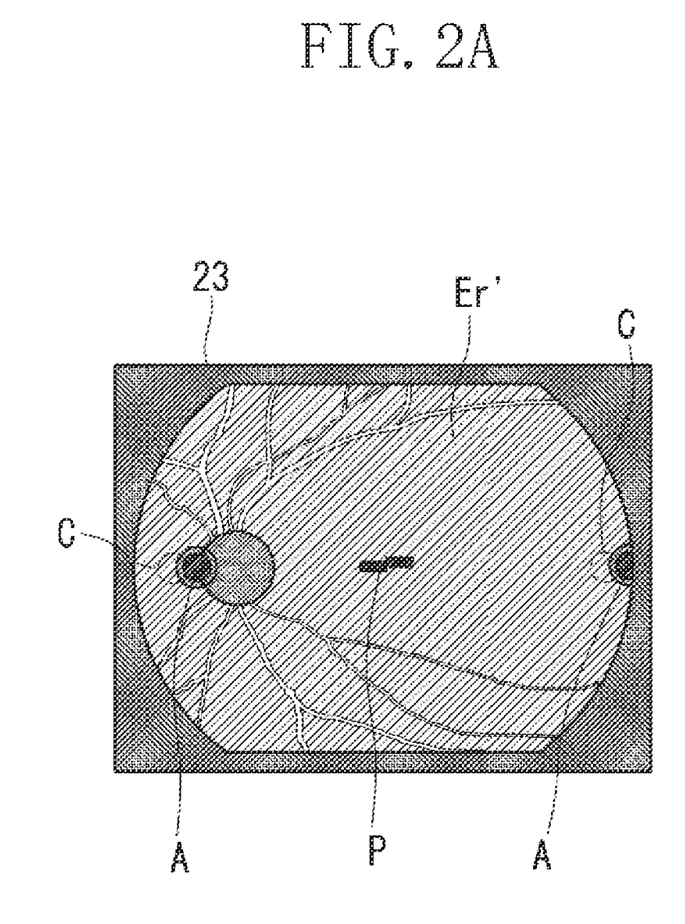
FIGS. 2A and 2B are observed images.
Figure 2B:
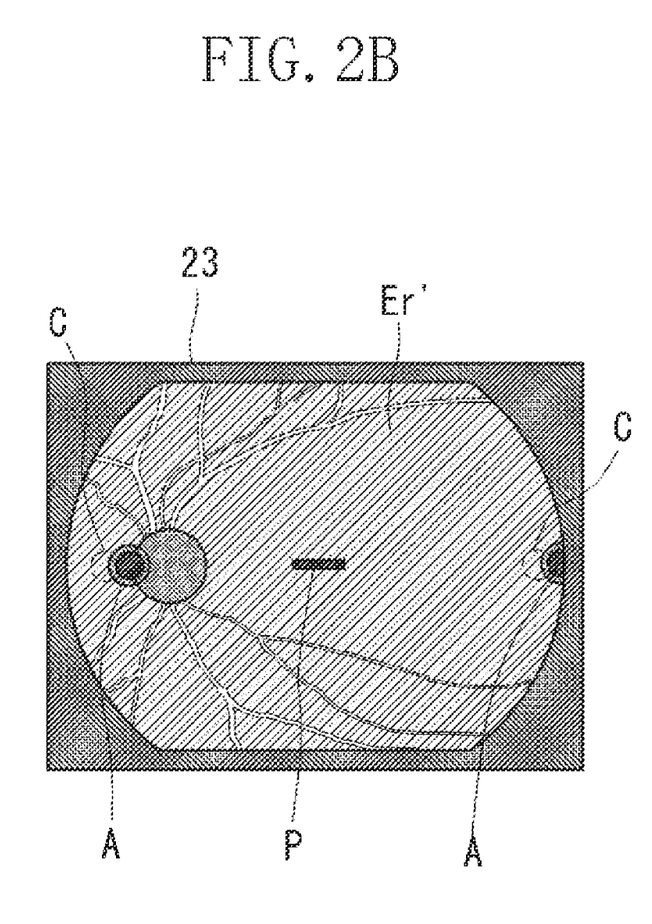

FIGS. 2A and 2B illustrates an observed state of the ocular fundus image Er' in the display unit 23. In FIG. 2A, a state is illustrated that none of the position adjustment and the focus adjustment have been completed yet, so that positioning circles C and positioning indexes A do not match to each other and a focus adjustment indexes P are also do not match to each other. In FIG. 2B, a state is illustrated that the position adjustment and the focus adjustment have been completed, so that the positioning circles C and the positioning indexes A match to each other and, the focus adjustment indexes P come to make a straight line.

The examiner presses a photographing switch of the operation switch unit 25 after the positioning adjustment and the focus adjustment of the ocular fundus image Er' are completed, so that the system control unit 22 cause the photographic light source 4 to emit light. A light flux emitted from the photographic light source 4 illuminates the ocular fundus Er while being transmitted through the same path as the light flux of the observation light source 1 is transmitted, and reflection light of the illuminated ocular fundus Er forms an image on the image sensor 15 in a similar manner as it was done upon observation of the image. Image data of the formed ocular fundus image Er' is transmitted to the image signal processing unit 21 and the system control unit 22, and stored in the image recording unit 24 as a color image while the color fundus image Er' is displayed on the display unit 23.

When autofluorescent observation is performed, the autofluorescent exciter filter 10 is inserted into the illuminating optical path. The light flux emitted from the observation light source 1 passes through the condenser lens 3 and the photographic light source 4 and is reflected by the mirror 5. The light reflected by the mirror 5 passes through the diaphragm 6 and the autofluorescent exciter filter 10 and is reflected at the area adjacent to the perforated mirror 9. The light further passes through the objective lens 2 and illuminates the ocular fundus Er with visible light.

The reflection light from the illuminated ocular fundus Er passes through an eye Ep, objective lens 2, the hole of the perforated mirror 9, the focusing lens 11, and the photographic lens 12, and forms an image on the image sensor 15. At the time, the autofluorescent barrier filter 14 is retreated from the ocular fundus observation and photographing optical system, so that the reflection light from the ocular fundus Er according to light of a wavelength which has passes through the autofluorescent exciter filter 10 can be observed as the ocular fundus image Er'.

The examiner performs, while observing the ocular fundus image Er', the position adjustment of the apparatus with respect to the subject's eye E with using the positioning indexes A and performs the focus adjustment with using the focus adjustment indexes P in the same manner as illustrated in FIG. 2.

The examiner presses the photographing switch of the operation switch unit 25 after completing the position adjustment and the focus adjustment of the ocular fundus image Er'. As a result, the system control unit 22 inserts the autofluorescent barrier filter 14 into the ocular fundus observation and photographing optical system and causes the photographic light source 4 to emit light. The light flux emitted from the photographic light source 4 passes through the optical path similar to the light flux of the observation light source 1 passes, and in the light flux, the light of wavelength which passes through the autofluorescent exciter filter 10 illuminates the ocular fundus Er. The reflection light from the illuminated ocular fundus Er passes through the eye Ep, the objective lens 2, the hole of the perforated mirror 9, the focusing lens 11, and the photographic lens 12, and thereafter the autofluorescent barrier filter 14 blocks the light of wavelength which is transmitted through the autofluorescent exciter filter 10. Accordingly, only the fluorescent of the ocular fundus image Er' passes through the autofluorescent barrier filter 14 to form an image on the image sensor 15.

Thus formed ocular fundus image Er' is converted into a monochromatic image by the image signal processing unit 21, transmitted to the system control unit 22, and stored in the image recording unit 24 as the monochromatic image. At the time, a monochromatic ocular fundus image Er' is displayed on the display unit 23.

In the color image photographing, there is arranged a tri-color separation color filter 16 in the image sensor 15 within the color photographing unit 13. In the tri-color separation color filter 16, a red (R) color, a green (G) color and a blue (B) color are arranged in mosaic shape so as to correspond to each of pixels. The image signal processing unit 21 reads out color data of each pixel through the filer from the image sensor 15, amplifies the color data, and calculates a virtual pixel value to form an image.

Figure 3:
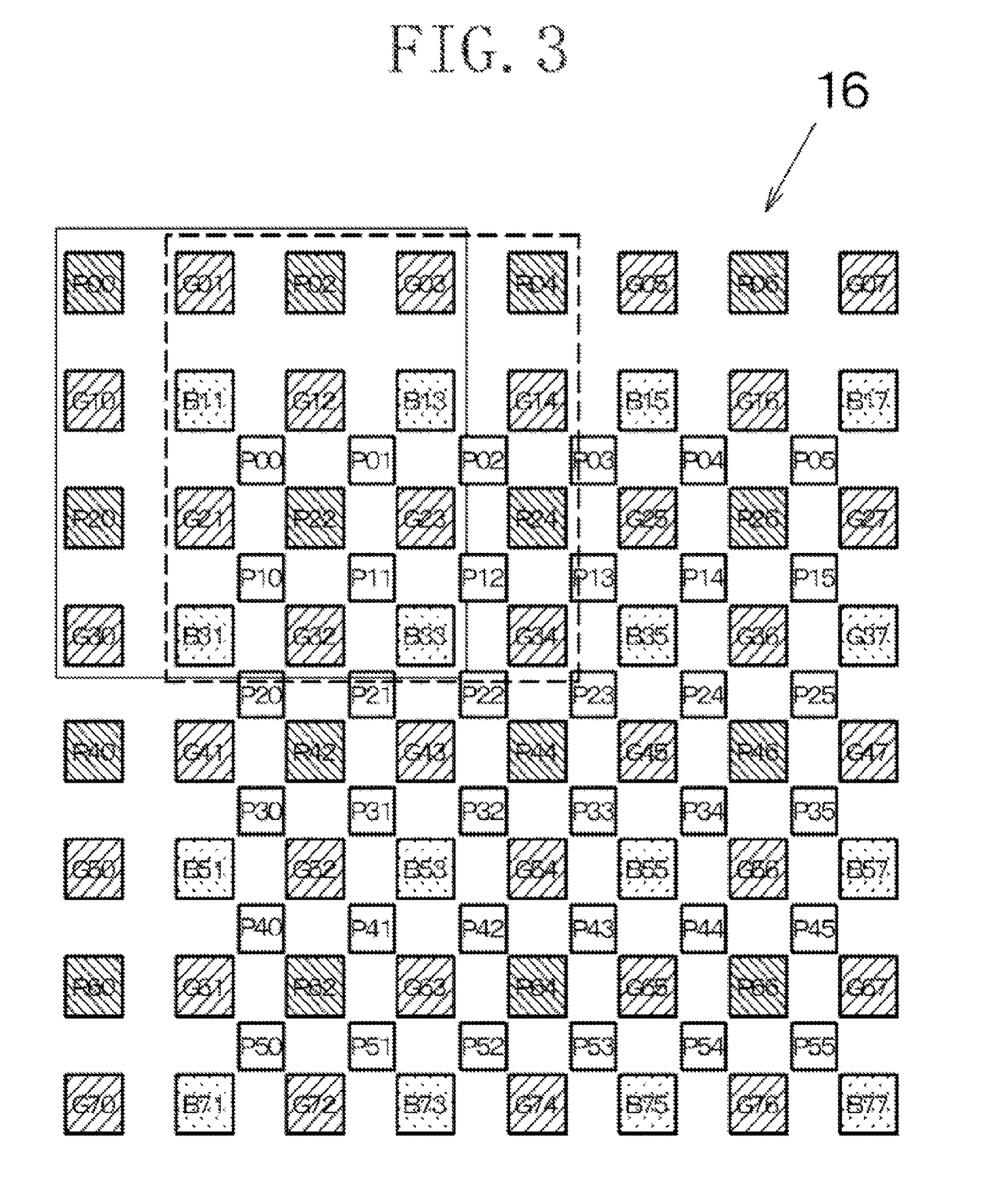
FIG. 3 is a schematic layout of a tri-color separation filter.

FIG. 3 illustrates a layout of a normal tri-color separation color filter 16. Calculation of a virtual pixel P00, when images are combined, is typically expressed as follows. A value of each colors of R, G and B of the virtual pixel P00 is calculated by the following formula based on received light data of pixels of R00, R02, B11, G12, B13, R20, G21, R22, B31 and B33 among the pixels adjacent to the virtual pixel P00 enclosed by a solid line.

In other words, assumed that the values of R, G and B of the virtual pixels are P00R, P00G and P00B, respectively, the calculation is performed according to a color dithering method.

$$P00G=(G12+G21)/2$$

$$P00R=(9*R22+3*R02+3*R20+R00)/16$$

$$P00B=(9*B11+3*B13+3*B31+B33)/16$$

The virtual pixel P01 right-next to the P00 is calculated by the following formula based on the received light data of pixels of R02, R04, B11, G12, B13, R22, G23, R24, B31 and B33 among the pixels in an area adjacent to the virtual pixel P01 enclosed in a dashed line.

$$P01G=(G12+G23)/2$$

$$P01R=(9*R22+3*R02+3*R24+R04)/16$$

$$P01B=(9*B13+3*B11+3*B33+B31)/16$$

Hereinafter, the virtual pixel values are calculated based on received light data of the pixels within the area of 4*4 adjacent to each of the virtual pixels P in the same manner, so that data of a piece of color image is generated.

Figure 4:
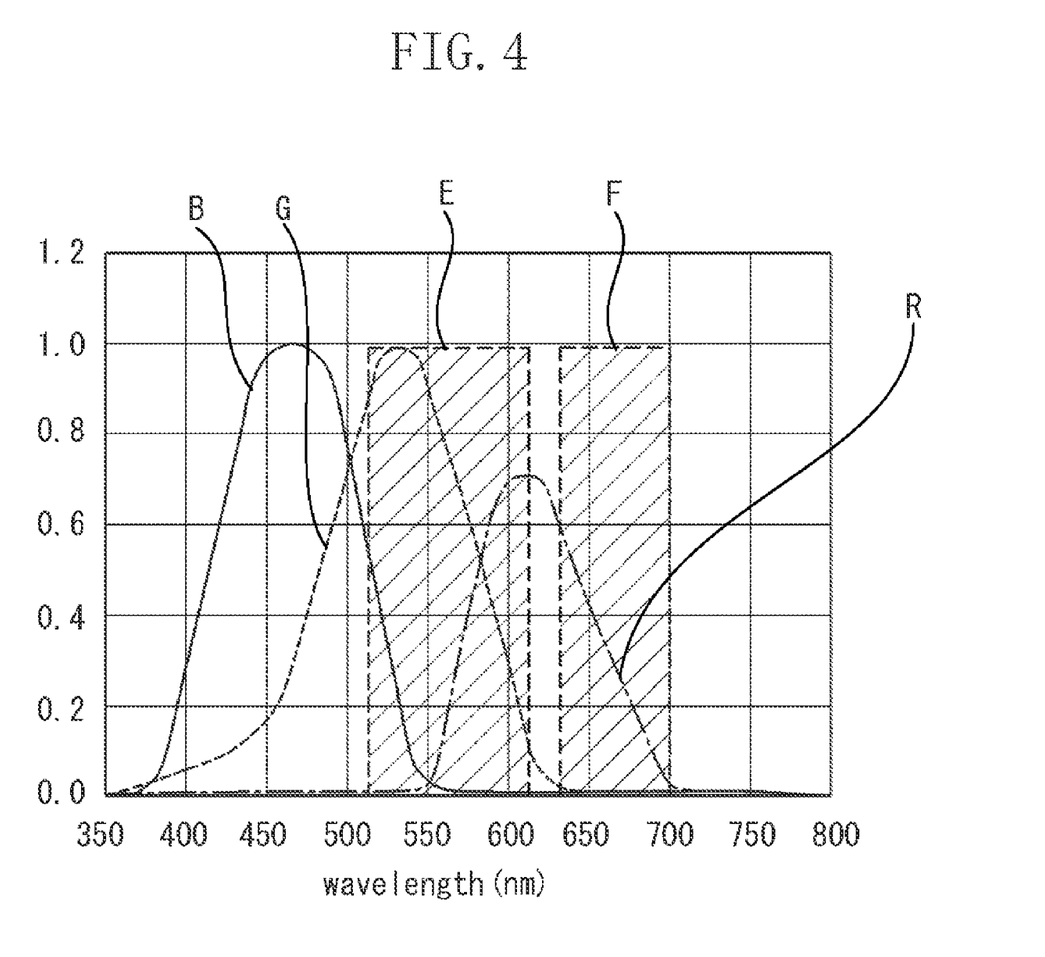
FIG. 4 illustrates spectral characteristics of color filters and autofluorescent filters.

FIG. 4 illustrates spectral characteristics according to the tri-color separation color filter 16 and the image sensor 15 of the color photographing unit 13. FIG. 4 further illustrates a characteristic E of the autofluorescent exciter filter 10 as a middle-bandwidth bandpass filter, a characteristic F of the autofluorescent barrier filter 14, a characteristic B of a blue filter as a narrow-bandwidth bandpass filter, a characteristic G of a green filter, and a characteristic R of a red filter. As it is seen from FIG. 4, the autofluorescent barrier filter 14 blocks light which is transmitted through the autofluorescent exciter filter 10.

Figure 5:
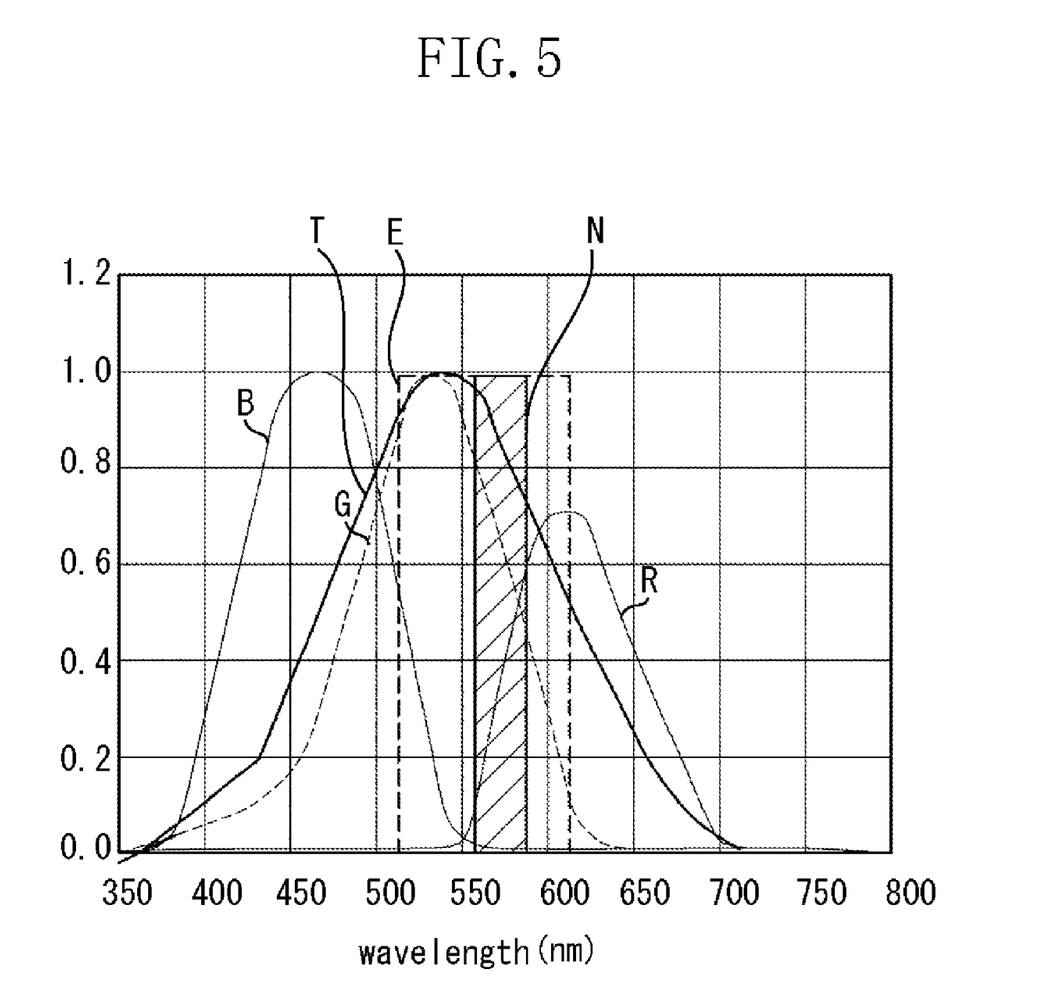
FIG. 5 illustrates spectral characteristics of a red free filter and a monochromatic conversion characteristic.

FIG. 5 is a spectral characteristic diagram illustrating a typical monochrome conversion characteristic T and a spectral characteristic N of the red free filter as the narrow-bandwidth bandpass filter.

As an example, the following formula is used to obtain an intensity Y of a monochromatic image from an RGB image using color data through a specific filter.

$$Y=0.299R+0.587G+0.114B \quad (1)$$

Figure 6:
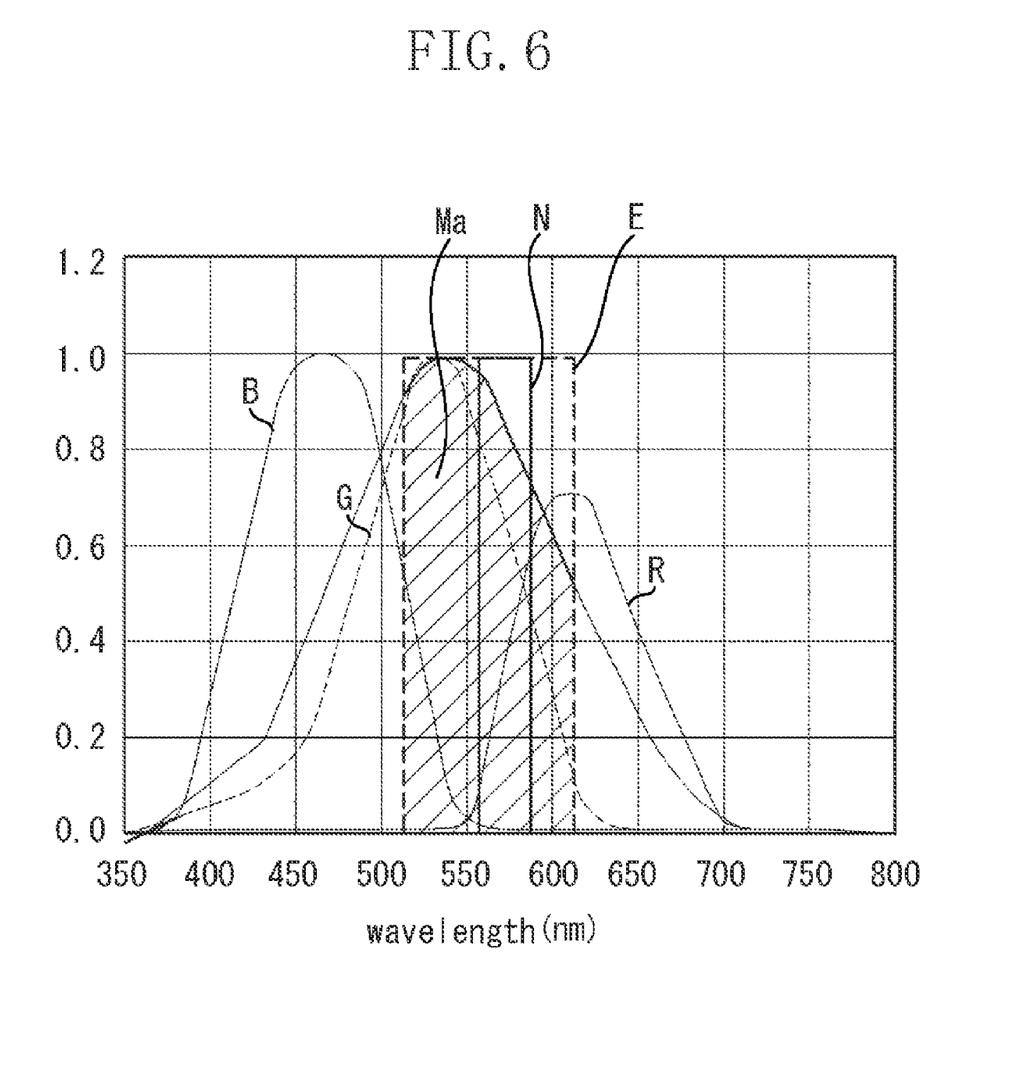
FIG. 6 illustrates spectral characteristics when converting into a monochromatic image through the autofluorescent filter.

FIG. 6 is a spectral characteristic diagram illustrating a spectral characteristic Ma, which is illustrated by hatching, of an image when a color ocular fundus image illuminated by the autofluorescent exciter filter 10 is converted into a monochromatic image according to the formula (1). In comparison with the spectral characteristic N of the red free filter, both of the bandwidths at a shorter wavelength side and a longer wavelength side are made wider.

Figure 7:
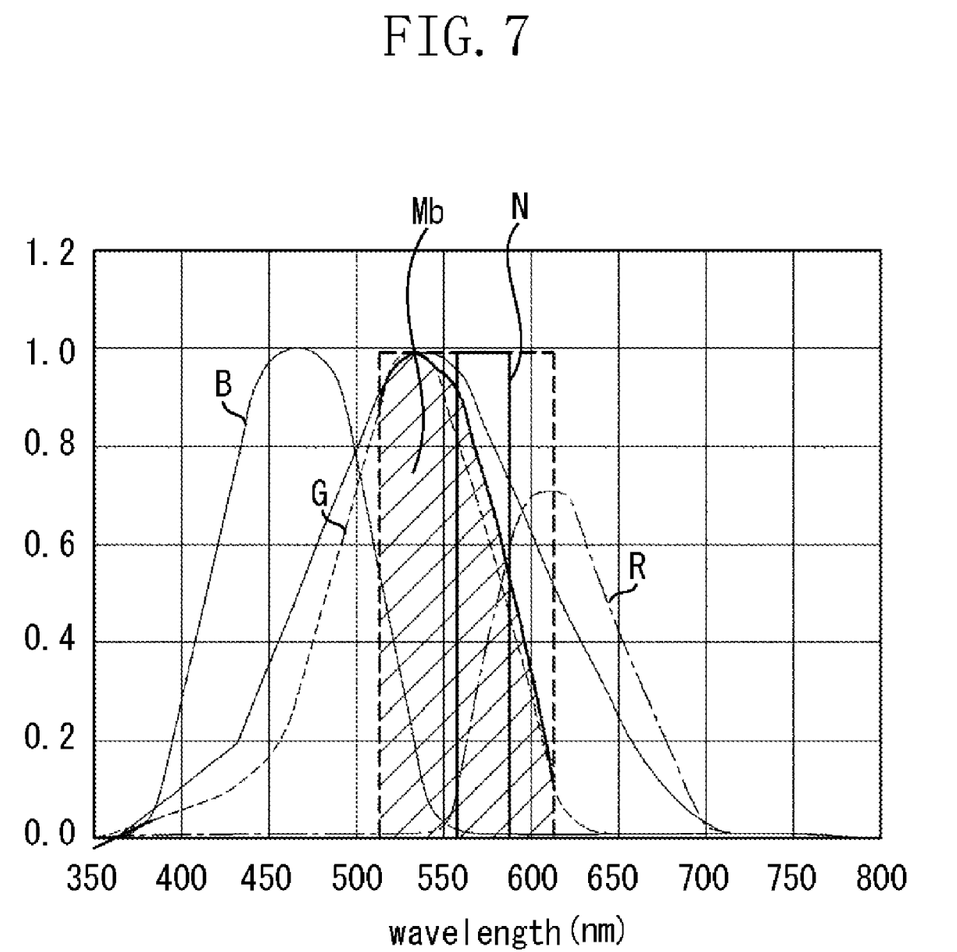
FIG. 7 illustrates spectral characteristics of a pseudo red free filter through a green filter.

FIG. 7 is a graph chart illustrating an effect of the present exemplary embodiment. In FIG. 7, the following formula is used in order to obtain the intensity Y using color data through the green filter.

$$Y=G \quad (2)$$

The spectral characteristic Mb corresponds to an image which is converted into a monochromatic image according to the formula (2) and when components of the longer wavelength side are reduced by using only color data through the green filter, an image having a characteristic similar to the characteristic N of the red free filter can be obtained.

As described above, the characteristic of the autofluorescent exciter filter 10 as the middle-bandwidth bandpass filter is combined with the characteristic of the tri-color separation color filter 16 of the color photographing unit 13. Accordingly, the pseudo spectral characteristic N of the red free filter can be realized without providing the red free filter as the narrow-bandwidth bandpass filter.

Figure 8:
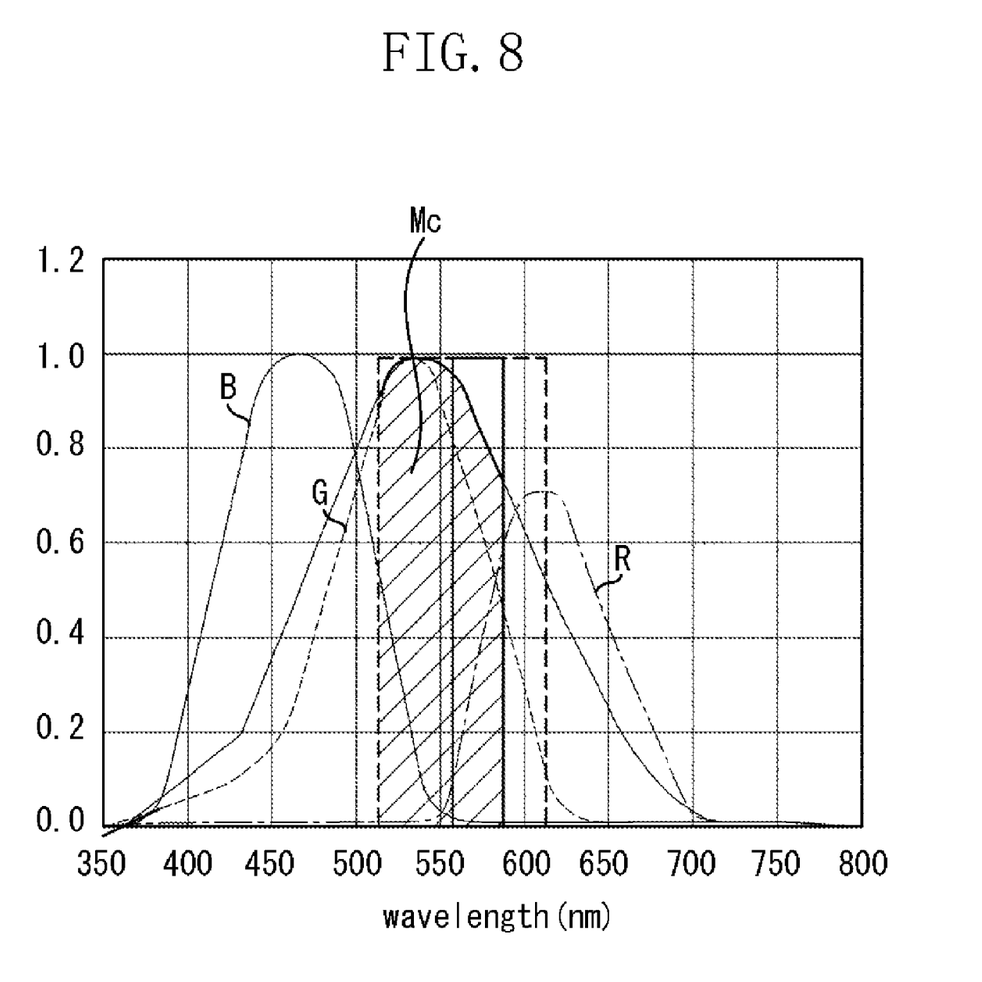
FIG. 8 illustrates spectral characteristics of the pseudo red free filter using a red/green (R/G) value.

FIG. 8 illustrates a spectral characteristic of the pseudo red free filter in which an R/G value when illuminated through a spontaneous luminescent filter is used. When the R/G, which is a ratio of the R value and the G value of each of the pixels of the captured color image, is equal to or more than a predetermined value, the value of each of the pixels is set to 0 or reduced to convert the captured color image into a monochromatic image according to the formula (1), so that the spectral characteristic Mc can be obtained, i.e., an image having a characteristic similar to the characteristic N of the red free filter can be obtained.

Figure 9:
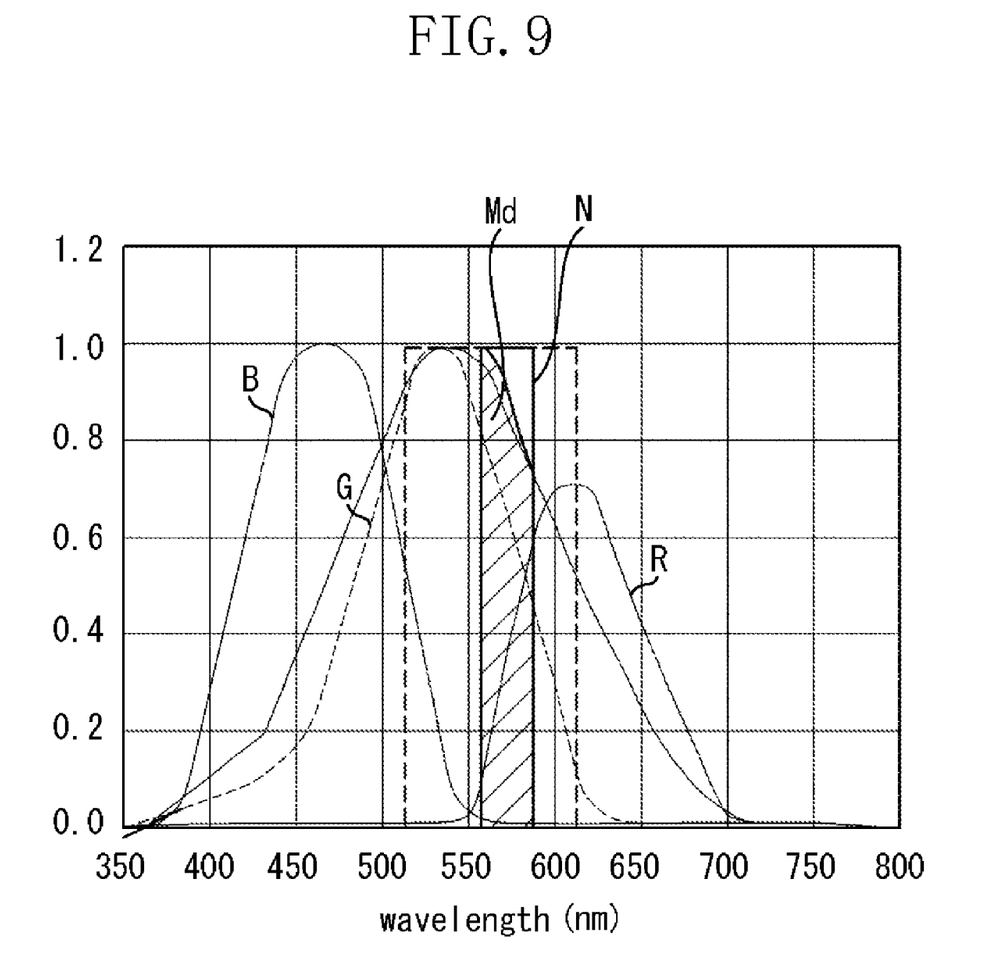
FIG. 9 illustrates spectral characteristic of the pseudo red free filter using the R/G value and a blue/green (B/G) value upon illumination through the autofluorescent filter.

FIG. 9 illustrates a spectral characteristic of the pseudo red free filter in which the R/G value and the B/G value when illuminated through the spontaneous luminescent filter is used. When the R/G, which is a ratio of the R value and the G value of each of the pixels of the captured RGB color image, is equal to or more than the predetermined value, the value of each of the pixels is set to 0 or reduced.

Further, the spectral characteristic Md can be obtained such that the image is converted into a monochromatic image according to the formula (1) after the value of each of the pixels is set to 0 or reduced when the B or the B/G is equal to or more than the predetermined value, and an image having a characteristic similar to the characteristic N of the red free filter can be obtained.

In the present exemplary embodiment, a single CCD type image sensor 15 is employed as the image sensor 15 within the color photographing unit 13. However, a 3CCD type image sensor can also be employed.

Figure 10:
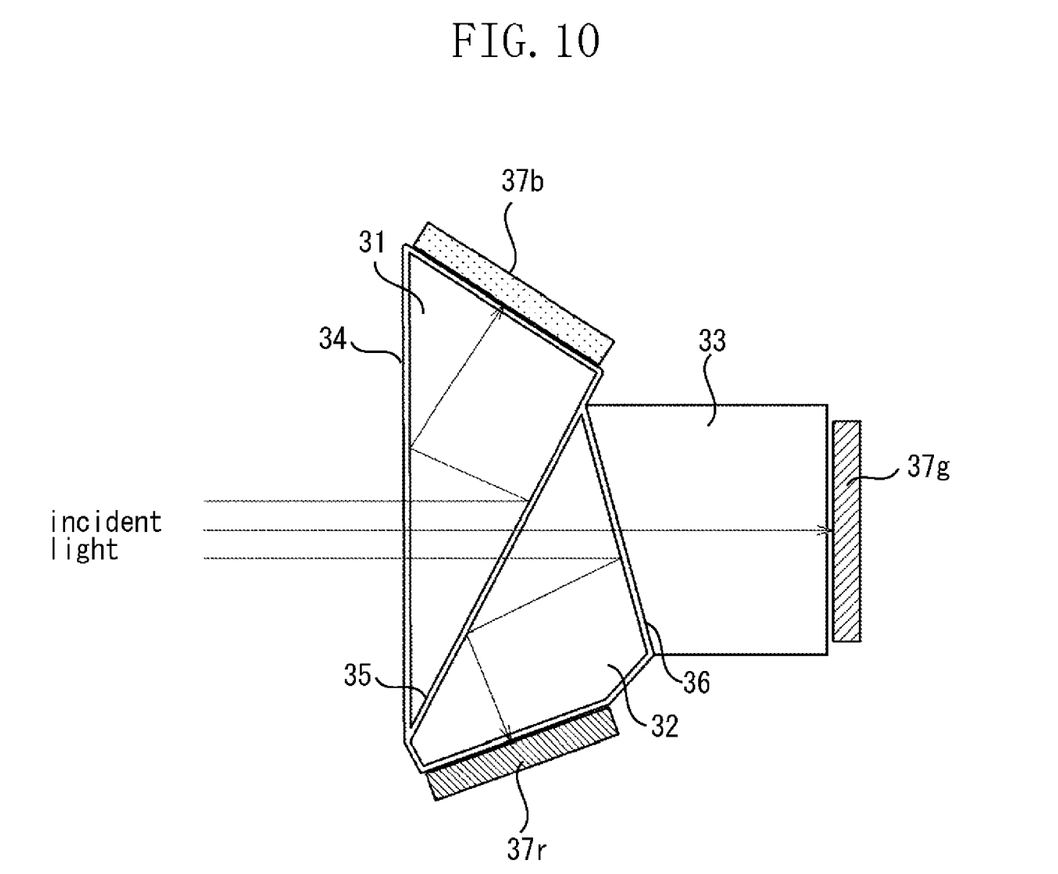
FIG. 10 illustrates a schematic layout of a 3 charge coupled device (CCD) type image sensor.

When using the 3CCD type image sensor, three spectral prisms 31, 32 and 33 are arranged as illustrated in FIG. 10 instead of the tri-color separation color filter 16 placed in front of the image sensor. Surfaces of the spectral prisms 31, 32 and 33 are provided with dichroic films 34, 35 and 36, respectively, and light is reflected and separated into three primary colors of RGB. Each of the image sensors 37b, 37r and 37g corresponding to the respective RGB colors is arranged on each of light exit surface of the spectral prisms 31, 32 and 33. Output from each of the image sensors 37b, 37r and 37g is taken into the image signal processing unit 21 to produce an equivalent effect as it is produced by the tri-color separation color filter 16.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-132356 filed Jun. 1, 2009, which is hereby incorporated by reference herein in its entirety

What is claimed is:

1. A fundus camera comprising:
an illumination unit configured to illuminate an ocular fundus of a subject's eye;
an autofluorescent exciter filter configured to be insertable into and retractable from an illumination optical path of the illumination unit;
an observation and photographing unit configured to receive reflection light from the ocular fundus illuminated by the illumination unit and form an ocular fundus image;
an autofluorescent barrier filter configured to be insertable into and retractable from an observation and photographing optical path of the observation and photographing unit;
an image capturing unit configured to capture an ocular fundus image formed by the observation and photographing unit; and
a calculation unit configured to calculate image data from the image capturing unit;
wherein the calculation unit of the fundus camera which can perform both of color image photographing and photofluorography, converts the ocular fundus image which is illuminated using the autofluorescent exciter filter inserted into the illumination unit and captured by a color image capturing unit as a color image, in a state that no autofluorescent barrier filter is inserted into the observation and photographing unit, into a monochromatic image from specific color data of the color image.

2. The fundus camera according to claim 1, wherein the calculation unit forms a monochromatic image which is obtained by an effect of a pseudo narrow-bandwidth bandpass filter.

3. The fundus camera according to claim 2, wherein an effect of a pseudo red free filter can be obtained such that the image capturing unit forms an RGB color image and the calculation unit converts the RGB color image into a monochromatic image using color data of a green filter.

4. The fundus camera according to claim 2, wherein an effect of a pseudo red free filter can be obtained such that the image capturing unit forms an RGB color image and the calculation unit converts the RGB color image into a monochromatic image from the adjacent color data of spectral characteristics of only red and green, red and green, or blue and green of each of pixels.

* * * * *